US006897024B2

(12) United States Patent
Bussemakers et al.

(10) Patent No.: US 6,897,024 B2
(45) Date of Patent: May 24, 2005

(54) NUCLEIC ACID MOLECULES COMPRISING THE PROMOTER FOR PCA3, AND USES THEREOF

(75) Inventors: Marion J. Bussemakers, Nijmegen (NL); Gerald Verhaegh, Maden (NL); Jack A. Schalken, Nijmegen (NL)

(73) Assignee: Stichting Katholieke Universiteit more particularly The University Medical Centre Nijmegen (NL)

( * ) Notice: Subject to any disclaimer, the term of this patent is extended or adjusted under 35 U.S.C. 154(b) by 0 days.

(21) Appl. No.: 09/996,953

(22) Filed: Nov. 30, 2001

(65) Prior Publication Data

US 2003/0165850 A1 Sep. 4, 2003

(30) Foreign Application Priority Data

| May 31, 2001 | (JP) | ........................................ 2001-164963 |
| Sep. 7, 2001 | (CA) | ............................................. 2357073 |

(51) Int. Cl.$^7$ ................................................. C12Q 1/68
(52) U.S. Cl. ........................ 435/6; 435/320.1; 435/325; 435/252.33; 435/29; 536/24.5
(58) Field of Search ..................... 536/24.5; 435/320.1, 435/6, 29, 252.33, 325

(56) References Cited

U.S. PATENT DOCUMENTS

| 6,261,562 B1 | 7/2001 | Xu et al. |
| 6,262,245 B1 | 7/2001 | Xu et al. |
| 2002/0022248 A1 | 2/2002 | Xu et al. |
| 2002/0035244 A1 | 3/2002 | Cohen et al. |

FOREIGN PATENT DOCUMENTS

| EP | 0 160 228 | 11/1985 |
| EP | 0 520 794 | 12/1992 |
| WO | WO 94/09820 | 5/1994 |
| WO | WO 95/28498 | 10/1995 |
| WO | WO 96/14875 | 5/1996 |
| WO | WO 98/45420 | 10/1998 |
| WO | WO 00/04149 A2 | 1/2000 |
| WO | WO 01/25272 A2 | 4/2001 |
| WO | WO 01/25273 A2 | 4/2001 |
| WO | WO 01/34802 A2 | 5/2001 |
| WO | WO 01/51633 A2 | 7/2001 |
| WO | WO 01/60860 A2 | 8/2001 |
| WO | WO 01/73032 A2 | 10/2001 |
| WO | WO 02/24718 A1 | 3/2002 |
| WO | WO 02/30268 A2 | 4/2002 |

OTHER PUBLICATIONS

Verhaegh et al. J. Biol. Chem., vol. 275, No. 48 (2000) pp. 37496–37503.*
Tamimi, Y., et al., DiagnoGene PCA3 reliable NASBA based reagents for detecting PCA3 rnRNA, a recently described prostate marker, *Proc. Am. Assoc. Cancer Res.* 39:234 Poster Abstract (1998).

Bussemakers, M.J. and Isaacs, W.B., "Identification of Genes Associated with Phosphate Cancer Development," *Urol. Res.* 21:452, Abstract No. P42, Springer International (1993).

Bussemakers, M.J.G. and Isaacs, W.B., "Identification of Genes Associated with Cancer Development," *8th Annual Spring Meeting, Society for Basic Urologic Research*, one page. Society for Basic Urologic Research (1994).

Bussemakers, M.J.G., et al., "Identification of DD3: A New Gene Overexpressed in Prostatic Tumors," *Urol. Res*23:253, Abstract No. 0 36, Springer International (1995).

Bussemakers, M.J.G., et al., "DD3: A New Prostate Specific Marker, Overexpressed in Prostatic Tumors," *Fall Symposium, Society for Basic Urologlc Research*, one page, Society for Basic Urologic Research (1995).

Bussemakers, M.J.G., et al., "DD3: A New Prostate Specific Marker, Overexpressed in Prostatic Tumors," *Breast and Prostate Cancer: Basic Mechanisms*, Abstract No. 102, pp. 17 (1996).

Bussemakers, M.J.G., et al., "DD3: a new prostate specific marker, overexpressed in prostatic tumors," *Proc. Am. Assoc. Cancer Res. Ann. Meeting* 37:515, Abstract No. 3522, American Association for Cancer Research (1996).

Bussemakers, M.J.G., et al., "DD3: A New Prostate Specific Marker, Overexpressed in Prostatic Tumors," *Meeting for the Dutch Association for Tumor Cell Biology* (1996).

Bussemakers, M.J.G., et al., "DD3: A New Prostate–Specific Marker, Strongly Overexpressed in Prostatic Tumors," *Urol. Res.* 25:76, Abstract No. 02.2, Springer International (1997).

Bowie, J.U., "Deciphering the Message in Protein Sequences: Tolerance to Amino Acid Substitutions," *Science* 247:1306–1311, American Association for the Advancement of Science (1990).

(Continued)

*Primary Examiner*—James Ketter
(74) *Attorney, Agent, or Firm*—Sterne, Kessler, Goldstein & Fox P.L.L.C.

(57) ABSTRACT

This invention describes the cloning and characterization of the promoter region for the PCA3$^{dd3}$ gene. This region regulates the PCA3$^{dd3}$ gene expression by a unique prostate specific transcriptional mechanism. The present invention relates to the use of this promoter region as a tool for prostate cancer treatment and diagnosis and screening of agents which regulate expression of PCA3. In a particular embodiment, the present invention relates to an isolated promoter sequence which comprises an isolated promoter sequence which comprises a sequence as set forth between nucleotide positions 372 to 460 of SEQ ID NO:1, this sequence enabling a prostate-specific modulation of transcription.

15 Claims, 6 Drawing Sheets

OTHER PUBLICATIONS

Burgess, W.H., et al., "Possible Dissociation of the Heparin–binding and Mitogenic Activities of Heparin–binding (Acidic Fibroblast) Growth Factor–1 from Its Receptor–binding Activities by Site–directed Mutagenesis of a Single Lysine Residue," *J. Cell Biol.* 111:2129–2138, The Rockefeller University Press (1990).

Gandini, O., "Is DD3 a New Prostate–specific Gene?," *Anticancer Res.* 23:305–308, J.G. Delinassios (Jan.–Feb. 2003).

Lazar, E., et al., "Transforming Growth Factor α: Mutation of Aspartic Acid 47 and Leucine 48 Results in Different Biological Activities," *Mol. Cell. Biol.* 8:1247–1252, American Society for Microbiology (1988).

Co–Pending U.S. Appl. No. 09/675,650, Busse, et al., filed Sep. 29, 2000 (Not Published).

Co–Pending U.S. Appl. No. 60/445,436, filed Feb. 7, 2003 (Not Published).

Co–Pending U.S. Appl. No. 09/402,713, Bussemakers, M.J., filed Oct. 8, 1999 (Published).

Altschul, S.F. et al., "Gapped Blast and PSI–Blast: a new generation of protein database search programs," *Nucl. Acids. Res.* 25:3389–3402, Oxford University Press (1997).

Boulikas, T., "Gene Therapy of Prostate Cancer: p53, Suicidal Genes, and Other Targets," *Anticancer Res.* 17:1471–1505, International Institute of Anticancer Research (1997).

Brakebusch, C. et al., "Expression of the 90K Immunostimulator Gene Is Controlled by a Promoter with Unique Features," *J. Biol. Chem.* 272:3674–3682, The American Society for Biochemistry and Molecular Biology, Inc. (1997).

Bussemakers, M.J.G. et al., "DD3: A New Prostate–specific Gene, Highly Overexpressed in Prostate Cancer," *Cancer Res.* 59:5975–5979, The American Association for Cancer Research (1999).

Bussemakers, M.J.G., "Changes in Gene Expression and Targets for Therapy," *Eur. Urol.* 35:408–412, S. Karger AG (1999).

Cleutjens, K.B.J.M. et al., "An Androgen Response Element in a Far Upstream Enhancer Region Is Essential for High, Androgen–Regulated Activity of the Prostate–Specific Antigen Promoter," *Mol. Endocrinol.* 11:148–161, The Endocrine Society (1997).

Cleutjens, K.B.J.M. et al., "A 6–kb Promoter Fragment Mimics in Transgenic Mice the Prostate–Specific and Androgen–Regulated Expression of the Endogenous Prostate–Specific Antigen Gene in Humans," *Mol. Endocrinol.* 11:1256–1265, The Endocrine Society (1997).

Gotoh, A. et al., "Development of Prostate–Specific Antigen Promoter–Based Gene Therapy For Androgen–Independent Human Prostate Cancer," *J. Urol.* 160:220–229, American Urological Association, Inc. (1998).

Hsing, A.W. et al., "International Trends and Patterns of Prostate Cancer Incidence and Mortality," *Int. J. Cancer (Pred. Oncol.)* 85:60–67, Wiley–Liss, Inc. (Jan. 2000).

Landis, S.H. et al., "Cancer Statistics, 1999," *CA Cancer J. Clin.* 49:8–31, American Cancer Society (1999).

Martiniello–Wilks, R. et al., "In Vivo Gene Therapy for Prostate Cancer: Preclinical Evaluation of Two Different Enzyme–Directed Prodrug Therapy Systems Delivered by Identical Adenovirus Vectors," *Human Gene Therapy* 9:1617–1626, Mary Ann Liebert, Inc. (1998).

Millikan, R.E., "Chemotherapy of Advanced Prostatic Carcinoma," *Semin. Oncol.* 26:185–191, W.B. Sauders Company (1999).

Pang, S. et al., "Identification of a Positive Regulatory Element Responsible for Tissue–specific Expression of Prostate–specific Antigen," *Cancer Res.* 57:495–499, The American Association for Cancer Research (1997).

Quandt, K. et al., "MatInd and MatInspector: new fast and versatile tools for detection of consensus matches in nucleotide sequence data," *Nucl. Acids. Res.* 23:4878–4884, Oxford University Press (1995).

Schalken, J., "Molecular Diagnostics and Therapy of Prostate Cancer: New Avenues," *Eur. Urol.* 34(suppl 3):3–6, S. Karger AG (1998).

Schuur, E.R. et al., "Prostate–specific Antigen Expression Is Regulated by an Upstream Enhancer," *J. Biol. Chem.* 271:7043–7051, The American Society for Biochemistry and Molecular Biology, Inc. (1996).

Taneja, S.S. et al., "Gene Therapy: Principles and Potential," in *Cancer Surveys 23: Preventing Prostate Cancer: Screening versus Chemoprevention*, Oliver, R.T.D. et al., eds., Cold Spring Harbor Laboratory Press, pp. 247–266 (1995).

Wei, C. et al., "Tissue–specific expression of the human prostate–specific antigen gene in transgenic mice: Implications for tolerance and immunotherapy," *Proc. Natl. Acad. Sci. USA* 94:6369–6374, The National Academy of Sciences of the USA (1997).

* cited by examiner

SEQ ID NO 1: PCA3$^{dd3}$ promoter and exon 1

```
-460  CACTAGAGGA GCACCTTAGG AATTGACCTG TGGATCTCAA CTTCGTTAGG

-410  GTTAAAAGAT TATTTGTTGG GCAAGGGTAG GACCAATAAC CTCATTCACA
                        C/EBPβ              CAAT box
-360  ATGCATTCAT TGATTCGTTG ATTCACAGAG CAAATACTTC TGAACAACTC -310  CTGTGTTTCT GGCACTGTTC TAGGCACCAG TGATATAGGA GCCAACAAGA
           Th1/E47
-260  CAGACATGTC ACTGCTCTCA TGGAGCTGCA TTTCAGTGCA TGGAGGCAGA -210  AAACAAACAA ACAAATAAAT AAATAAATAA ATAAATAAGA TAATTTTTAA
                          FREAC-7/FKHL11
-160  TAGCAACGTG TCAACATAGT GTGACGGGAA GGAGCATGAT GAGACAGAAG

-110  GAAGGTTTAA ACTGGGAAAT CTGAGAAATG GTATGGTTGT ATGTGGGTTG

-60   GCATTCTTGC ATGATGGGAG TGGCCACCTG CTTTCATATT CTGAAGTCAG
      NF-1                      E-box
-10   AGTGTTCCAG ACAGAAGAAA TAGCAAGTGC CGAGAAGCTG GCATCAGAAA
                   *                     exon 1
 41   AACAGAGGGG AGATTTGTGT GGCTGCAGCC GAGGGAGACC AGGAAGATCT
                              exon 1
 91   GCATGGTGGG AAGGACCTGA TGATACAGAG  120
                    exon 1
```

FIGURE 2

SEQ ID NO 2: PCA3$^{dd3}$ specific antisens oligonucleotide BUS2

5'-CTCTGTATCATCAGGTCCTTCC-3'

SEQ ID NO 3: PCA3$^{dd3}$ specific antisens oligonucleotide BUS7

5'-CTGGAAATGTGCAAAAACAT-3'

SEQ ID NO 4: PCA3$^{dd3}$ specific oligonucleotide BUS21

5'-CCTTCCCACCATGCAGATCTTCCTGGTCTCCCTCGGCTGCAGCCACACAA-3'

NUCLEIC ACID MOLECULES COMPRISING THE PROMOTER FOR PCA3, AND USES THEREOF

CROSS-REFERENCE TO RELATED APPLICATIONS

This application claims priority to the following applications: Japanese Patent Application No. 2001-164963, filed May 31, 2001 and Canadian Patent Application No. 2,357,073, filed Sep. 7, 2001, both of which are specifically incorporated herein by reference in their entirety.

FIELD OF THE INVENTION

The present invention relates to prostate cancer. More precisely, the present invention relates to nucleic acid molecules, which have been isolated and characterized as the promoter for PCA3$^{dd3}$, a new prostate cancer antigen. This invention related also to different methods based on the use of recombinant DNA technology for prostate tumor diagnosis, prevention, therapy and the like.

BACKGROUND OF THE INVENTION

In the United States, according to statistical data published in 1999 by Landis et al. (CA Cancer J. Clin. 49:8–31 (1999)), prostate cancer is the most commonly diagnosed cancer and the second leading cause of cancer death, following lung cancer, in men. These results are not specific to the United States as they characterize all western countries. In addition incidence for this cancer is rising rapidly in most countries including low-risk populations, namely populations from Asian countries (Hsing et al., Int. J. Cancer 85:60–67 (2000)).

There is at present no effective treatment available for patients with advanced and/or hormone-insensitive prostate cancer. Therapeutic modalities for advanced prostate cancer are limited to drugs with considerable toxicity.

As the proliferation rate is low in these cancers, many cytotoxic agents are ineffective (Millikan, Semin. Oncol. 26(2):185–191 (1999)). Thus there is an urgent need to develop new approaches to treat patients with progressive prostate cancer. For example, gene therapy can be done using prostate-specific gene promoters linked to genes that suppress tumor cell growth, induce apoptosis and/or kill tumor cells (Taneja et al., Cancer Surv. 23:247–266 (1995); and Boulikas, Anticancer Res. 17:1471–1505 (1997)). The promoter sequences responsible for the prostate specific expression of several genes have been cloned and the unraveling of their transcriptional regulation is ongoing. The PSA gene promoter has been most extensively studied and revealed the existence of a proximal prostate-specific promoter with an upstream prostate-specific enhancer. Both sequences are required for high, androgen-regulated activation of PSA expression (Schuur et al., J. Biol. Chem. 271:7043–7051 (1996); Cleutjens et al., Mol. Endocrinol. 11:148–161 (1997); Cleutjens et al., Mol. Endocrinol. 11:1256–1265 (1997); Pang et al., Cancer Res. 57:495–499 (1997); and Wei et al., Proc. Natl. Acad. Sci. USA 94:6369–6374 (1997)). Using the PSA enhancer-promoter linked up to the HSV-tk gene, encoding a prodrug-converting enzyme and delivered by the human adenovirus into prostatic tumor cells growing subcutaneously in nude mice, it has been shown that prostate tumor cell growth was significantly suppressed and that the life span of the animals was prolonged (Gotoh et al., J. Urol. 160:220–229 (1998); and Martiniello-Wilks et al., Hum. Gene Ther. 9(11):1617–1626 (1998)). This proof of principle opens the way for application of promoter-based gene therapy for prostate cancer patients.

A new candidate marker for prostate cancer was discovered a few years ago by differential display analysis intended to highlight genes associated with prostate cancer development. This new gene was named PCA3 and also DD3 (Bussemakers, PCT/CA98/00346, published as WO 98/45420 (1998), Schalken, Eur. Urol. 34(suppl. 3):3–6 (1998), Bussemakers et al., Cancer Res. 59:5975–5979 (1999) and Bussemakers, Eur. Urol. 35:408–412 (1999)). PCA3$^{dd3}$ is located on chromosome 9 and more precisely to region 9q21–22. It consists of four exons, which give rise, by both alternative splicing and alternative polyadenylation, to differently sized transcripts. By RT-PCR, PCA3$^{dd3}$ expression was found to be limited to the prostate tissue and absent in all other tissues tested, including testis, seminal vesicle, ovary, placenta and bladder. In addition northern blot analysis showed that PCA3$^{dd3}$ is highly expressed in the vast majority of prostate cancer examined (47 out of 50) whereas no or very low expression is detected in BPH or normal prostate cells from the same patients. Of note, there is at least a 20-fold over-expression of PCA3$^{dd3}$ in prostate carcinoma in comparison to normal or BPH tissues. PCA3$^{dd3}$ expression seems to increase with tumor grade and is detected in metastatic lesions.

There thus remains a need to identify the promoter responsible for regulation and expression of PCA3$^{dd3}$. There also remains a need to provide regulatory sequences which are prostate cancer tissue specific and to use such sequences to diagnose, prevent or treat prostate cancer.

The present invention seeks to meet these and other needs.

The present description refers to a number of documents, the content of which is herein incorporated by reference in their entirety.

DEPOSIT OF NUCLEOTIDE SEQUENCE

The nucleotide sequence for the PCA3$^{dd3}$ promoter region was deposited into the GenBank™ database under the accession number AF279290.

SUMMARY OF THE INVENTION

The invention concerns the identification of the promoter sequence for PCA3$^{dd3}$ gene. This gene is a new prostate cancer marker, which overcomes many if not all of the drawbacks of the prostate marker of the prior art. The characterization of this promoter is a very useful tool for the development of new strategies in order to treat, for example, patients having defects, diseases or damages in prostatic cells and especially of patients with advanced prostate cancer, and particularly androgen-insensitive prostate cancer. Having identified PCA3$^{dd3}$ as a marker for prostate cancer, and having now identified the promoter thereof, the present invention provides the means to prevent the progression of the cancer into higher grades as well as to revert the cancerous state of the prostate tumor.

The present invention further relates to the discovery and characterization of the novel prostate specific promoter sequence of the PCA3$^{dd3}$ gene, which enables a prostate tissue specific expression of a heterologous sequence.

The invention in addition provides a recombinant nucleic acid molecule comprising, 5' to 3', a prostate specific promoter effective to initiate transcription in a prostate host cell and a heterologous DNA sequence of interest. In one embodiment of the present invention, the prostate cancer specific promoter is the PCA3$^{dd3}$ promoter as defined in FIG. 1, between position −460 to +62 (position 1 to 522 in SEQ ID NO:1). However, sequence polymorphisms may exist. In addition, sub-regions and variants of this sequence may be used in accordance with the present invention, provided that such sub-regions or variants retain their biological activity in enabling a prostate cancer-specific tissue expression of the sequences operably linked thereto. Indeed, as exemplified hereinbelow, sub-regions of this −460 to +62 nucleic acid region still retain prostatic tissue promoter activity.

The invention also provides a recombinant vector comprising one of the above-described PCA3$^{dd3}$ promoter sequences and a heterologous sequence operably linked thereto.

The invention also provides a cell that contains an above-described recombinant vector.

Figure 1:
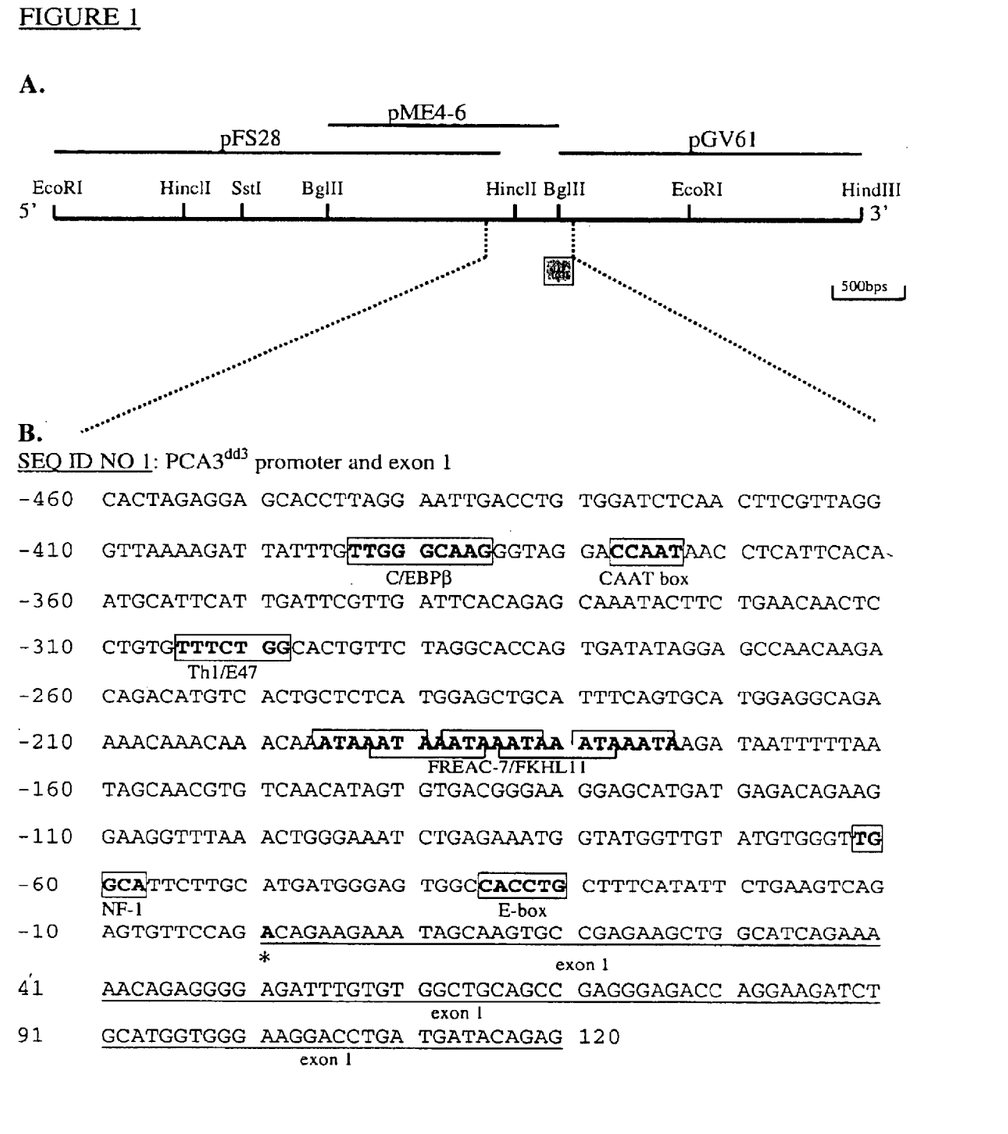

The invention further includes antisense nucleic acid molecules or ribozymes specific to the PCA$^{dd3}$ promoter sequences of the present invention, so as to enable a modulation of the expression of the PCA3$^{dd3}$ promoter and thus of the sequence operably linked thereto (e.g. the PCA3 coding sequences). In one particular embodiment, this antisense comprises a sequence which is complementary to the sequence spanning nucleotides −70 to −30 as shown in FIG. 1 (position 391 to 431 of SEQ ID NO:1). Antisense sequences complementary to the other promoter sequences of the present invention are also within the scope of the present invention.

The invention further relates to a non-human organism that contains an above-described recombinant vector. In particular, the invention relates to a non-human organism containing a recombinant vector comprising a PCA3$^{dd3}$ promoter sequence operably linked to a heterologous sequence. In a particular embodiment, the promoter sequence comprises a sequence as set forth in FIG. 1, between position −460 to +62 (position 1 to 522 in SEQ ID NO:1), variants of parts thereof.

The invention provides, in general, isolated nucleic acid molecules enabling a prostatic tissue specific expression of a heterologous sequence and to variants or portions thereof, retaining their ability to enable a prostate tissue specific expression thereof.

The invention also provides methods for therapeutic uses involving all or part of a nucleic acid sequence encoding the PCA3$^{dd3}$ promoter according to the present invention, variants or parts thereof, operably linked to a heterologous sequence.

Having identified and characterized the PCA3$^{dd3}$ promoter and having determined and characterized regions thereof which retain their tissue-specific promoter expression enables the design of diagnostic methods to determine the promoter activity of PCA3$^{dd3}$ and hence the cancer-predisposing or cancer status of the sample from which the promoter activity is assessed. A number of methods for determining a promoter activity are available and known to a person of ordinary skill. A non-limiting example of such a diagnostic method to determine the promoter activity of the PCA3$^{dd3}$ promoter in a sample from a patient can be performed by PCR analysis of the PCA3$^{dd3}$ promoter using primers which can distinguish between different methylation states of a sequence (i.e. CpG; Jarrard et al. 1998, Cancer Res. 58:5310–5314). Such methods could enable a diagnosis/prognosis of prostate cancer in a patient. Since sodium bisulfite transforms non-methylated cytosine into thymidine (methylated cytosine are not changed into thymidine), a design of PCR primers which can distinguish between a hypo- versus a hyper-methylated state of the promoter can be carried-out by a person of ordinary skill. The hypo-methylated state of the promoter (which correlate with an active state of the promoter) would indicate a cancerous state or predisposition thereto of the prostatic sample (e.g. the primer would have bound to a sequence in which the Cs would have been changed into Ts). Of course, other methods of determining the activity of a promoter can be carried-out.

The invention in addition relates to screening assays to identify agents which modulate the PCA3$^{dd3}$ promoter of the present invention comprising a comparison of the level of expression thereof in the presence as opposed to in the absence of a candidate agent. Such assays, which can be adapted by a person of ordinary skill, can be used to further dissect the structure function of the promoter sequence. One type of such assays is exemplified hereinbelow in order to more precisely define the sequences and/or boundaries of the PCA3$^{dd3}$ promoter.

Figure 7:
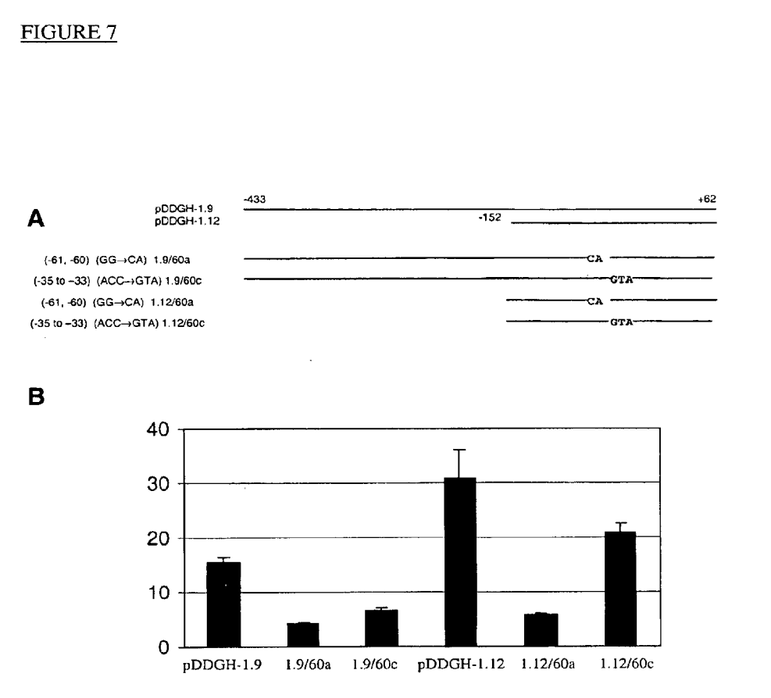
FIG. 7 shows the effects of site directed mutagenesis on the PCA3$^{dd3}$ promoter activity. (A) PCA3$^{dd3}$ minimal promoter constructs (pDDGH-1.9 and −1.12) are shown as lines with numbers corresponding to their positions relative to the transcription start site. Mutant constructs are shown below. The position of the mutations with respect to the transcription start site and the substituted bases are indicated to the left of each construct. (B) Promoter mutants were transiently transfected into LNCaP cells and hGH production and promoter activities were determined as described in FIG. 5.

As taught herein, a number of sequences from the PCA3$^{dd3}$ promoter are shown to retain the prostate-specific promoter activity (see FIG. 7). Thus, the present invention present a number of PCA3$^{dd3}$ promoter sequences which can be used to direct the expression of a chosen heterologous sequence. Since, as well known in the art, a promoter is defined as a DNA region involved in the binding of RNA polymerase to initiate transcription, the PCA3$^{dd3}$ promoter sequences characterized herein should not be limited to the DNA sequence which comprises the +2 to +62 region of FIG. 1 (position 462 to 522 in SEQ ID NO:1). Indeed, while most of the constructs used to characterize the promoter sequences included the +2 to +62 region, and hence the mRNA start site and beyond (all part of exon 1), it should be clear to the person of ordinary skill that the promoter sequences may end at the −1 position (nucleotide 460 in SEQ ID NO:1) (or +1 position if the transcription start site is included) as shown in FIG. 1. Thus, non-limiting examples of the PCA3$^{dd3}$ promoter sequences of the present invention include a PCA3$^{dd3}$ sequence comprising, with reference to FIG. 1, nucleotides −89 to −1, −89 to +1, −89 to +62; −152 to −1, −152 to +1, −152 to +62; −254 to −1, −254 to +1, −254 to +62; −366 −366 to +1, −366 to +62; or −433 to −1, −433 to +1, −433 to +62 (372 to 460, 372 to 461, 372 to 522, 309 to 460, 309 to 461, 309 to 522, 207 to 460, 207 to 461, 207 to 522, 95 to 460, 95 to 461, 95 to 522, 28 to 460, 28 to 461, 28 to 522 in SEQ ID NO:1, respectively). Of course, SEQ ID NO:1 is also within the scope of the present invention as well as the PCA3$^{dd3}$ sequence spanning −460 to −1, −460 to +1 or −460 to +62, in FIG. 1, or 1 to 460, 1 to 461 or 1 to 522 in SEQ ID NO:1.

In order to provide a clear and consistent understanding of terms used in the present description, a number of definitions are provided hereinbelow.

As used herein, the terminology "non-malignant prostate or status" is meant to cover a non-cancerous prostatic state. Thus, these terminologies are meant to include a normal status as well as a benign prostatic status (such as BPH, for example).

The terminology "therapeutic sequence" refers to a DNA sequence which indirectly or directly has an effect on the host cell in which it is expressed. Preferably, this therapeutic sequence encodes an amino acid sequence encoding a functional protein which is capable of displaying a therapeutic effect in the host cell in which the functional promoter activity of the PCA3$^{dd3}$ promoter enables expression of the therapeutic protein and the therapeutic effect of this protein is effected directly, or indirectly.

Figure 5:
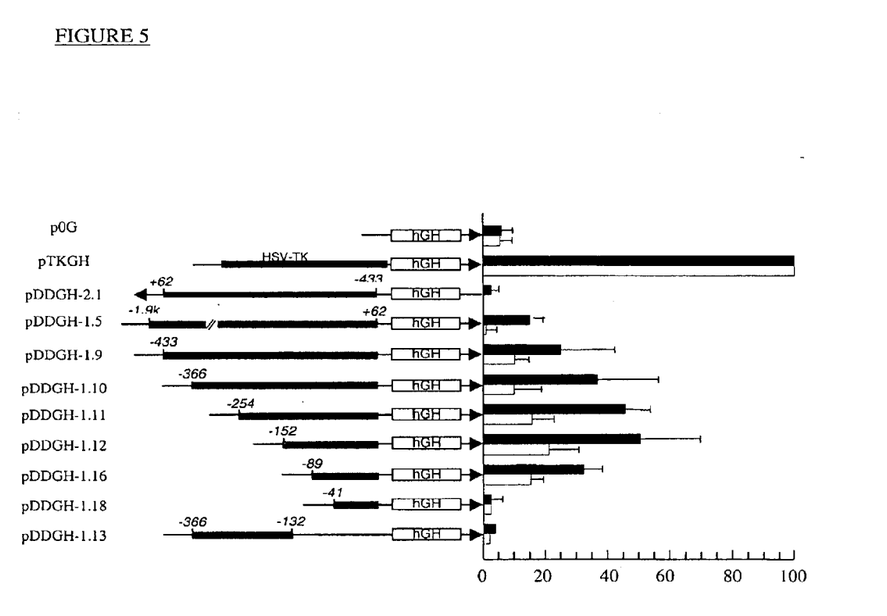
FIG. 5 shows the PCA3$^{dd3}$ promoter activity in the two human prostate cancer cell lines TSU-pr1 and LN-CaP after transient transfection. PCA3$^{dd3}$ promoter constructs used for transient transfections are shown at the left. Thin lines indicate vector sequences, boxes indicate the human growth hormone (hGH) gene, and the hatched boxes the PCA3$^{dd3}$ promoter fragments. Positions relative to the transcription initiation site are indicated. Human growth hormone production in LNCaP cells (PCA3$^{dd3}$-positive, black bars) and in TSU-pr1 cells (PCA3$^{dd3}$-negative, light bars) were calculated using pTKGH (hGH gene expression driven by the HSV-tk promoter) as a reference. Error bars indicate the standard error of the mean of three independent experiments done in duplicates.

The terminology "PCA3$^{dd3}$ promoter" refers to a sequence from the PCA3$^{dd3}$ promoter as shown in FIG. 1 or FIG. 5, or fragments or derivatives thereof, which retain their prostate tissue specific promoter activity.

The terminology "enhancer element" is meant to define a sequence which enhances the activity of a promoter (i.e. increases the rate of transcription of a sequence downstream of the promoter) which, as opposed to a promoter, does not possess promoter activity, and which can usually function irrespective of its location with respect to the promoter (i.e. upstream, or downstream of the promoter). In one embodiment, the isolated nucleic acid having promoter activity, as taught herein, may be combined with an enhancer element, so as to increase the transcriptional activity of the PCA3$^{dd3}$ promoter. Enhancer elements are well-known in the art. Non-limiting examples of enhancer elements (or parts thereof) which could be used to increase the promoter activity of the PCA3$^{dd3}$ promoter include enhancer elements found in retroviral LTRs (e.g. MMTV LTR), or SV40 enhancer sequences and the like.

As well-known in the art, having identified sequences having prostate tissue specific promoter activity, as well as important regions of the PCA3$^{dd3}$ promoter (e.g. NF-1 box and E-box), a person skilled in the art could modify the promoter in order to further increase its transcriptional activity. For example, (1) multiplying the number of sequences binding prostate cell- and especially prostate cancer cells-specific or regulatory proteins or factors which bind the different elements boxed in FIG. 1; (2) adding one or more enhancers, could significantly enhance the strength (i.e. the transcriptional activity) of the PCA3$^{dd3}$ promoter. Of course, such modifications should retain the prostate tissue-specific promoter activity of the PCA3$^{dd3}$ promoter sequences.

Numerous therapeutic genes are well-known in the art. A non-limiting list thereof can be found, for example, in U.S. Pat. No. 5,919,652. Therapeutically genes include, without being limited thereto, suicide genes, which when produced, will kill the host cell in which it is expressed. Suicide genes include, for example, enzymes, toxins, tumor suppressor genes and oncogenes. While the primary purpose of the suicide gene is to kill the host cell in which it is expressed, suicide gene could also inhibit the growth of the host cell. It will be understood that the inhibitory or killing effect of the suicide gene can be direct or indirect.

Non-limiting examples of therapeutic sequences which can be used in accordance of the present invention include TK, suitable oncogenes and tumor suppressor genes such as Ras, p53, Rb, Wilm's tumor gene, toxins such as diphteria toxin, bacterial toxins, tumor necrosis factors, interferons and the like.

Numerous vectors can be used in accordance with the present invention in order to express, through the influence of the PCA3$^{dd3}$ promoter, a chosen heterologous sequence, and more particularly, a therapeutic sequence. Such vectors are very well-known in the art. Non-limiting examples thereof include: adenovirus-based vectors, retroviral vectors, adeno-associated viral vectors (AAV), other human and animal viruses, SV40 and HSV-1 (see U.S. Pat. No. 5,919,652 for a more extensive list of non-limiting vectors which could be used in accordance with the present invention).

Nucleotide sequences are presented herein by single strand, in the 5' to 3' direction, from left to right, using the one letter nucleotide symbols as commonly used in the art and in accordance with the recommendations of the IUPAC-IUB Biochemical Nomenclature Commission.

Unless defined otherwise, the scientific and technological terms and nomenclature used herein have the same meaning as commonly understood by a person of ordinary skill to which this invention pertains. Generally, the procedures for cell cultures, infection, molecular biology methods and the like are common methods used in the art. Such standard techniques can be found in reference manuals such as for example Sambrook et al. (1989, Molecular Cloning -A Laboratory Manual, Cold Spring Harbor Laboratories) and Ausubel et al. (1994, Current Protocols in Molecular Biology, Wiley, N.Y.).

The present description refers to a number of routinely used recombinant DNA (rDNA) technology terms. Nevertheless, definitions of selected examples of such rDNA terms are provided for clarity and consistency.

As used herein, "nucleic acid molecule", refers to a polymer of nucleotides. Non-limiting examples thereof include DNA (i.e. genomic DNA, cDNA) and RNA molecules (i.e. mRNA) as well as chimeras thereof. The nucleic acid molecule can be obtained by cloning techniques or synthesized. DNA can be double-stranded or single-stranded (coding strand or non-coding strand [antisense]).

The term "recombinant DNA" as known in the art refers to a DNA molecule resulting from the joining of DNA segments. This is often referred to as genetic engineering.

The term "DNA segment", is used herein, to refer to a DNA molecule comprising a linear stretch or sequence of nucleotides. This sequence when read in accordance with the genetic code, can encode a linear stretch or sequence of amino acids which can be referred to as a polypeptide, protein, protein fragment and the like.

The terminology "amplification pair" refers herein to a pair of oligonucleotides (oligos) of the present invention, which are selected to be used together in amplifying a selected nucleic acid sequence by one of a number of types of amplification processes, preferably a polymerase chain reaction. Other types of amplification processes include ligase chain reaction, strand displacement amplification, or nucleic acid sequence-based amplification, as explained in greater detail below. As commonly known in the art, the oligos are designed to bind to a complementary sequence under selected conditions.

The nucleic acid (i.e. DNA or RNA) for practicing the present invention may be obtained according to well known methods.

Oligonucleotide probes or primers of the present invention may be of any suitable length, depending on the particular assay format and the particular needs and targeted genomes employed. In general, the oligonucleotide probes or primers are at least 12 nucleotides in length, preferably between 15 and 24 molecules, and they may be adapted to be especially suited to a chosen nucleic acid amplification system. As commonly known in the art, the oligonucleotide probes and primers can be designed by taking into consideration the melting point of hydrizization thereof with its targeted sequence (see below and in Sambrook et al., 1989, Molecular Cloning -A Laboratory Manual, 2nd Edition, CSH Laboratories; Ausubel et al., 1989, in Current Protocols in Molecular Biology, John Wiley & Sons Inc., N.Y.).

The term "oligonucleotide" or "DNA" molecule or sequence refers to a molecule comprised in general of the deoxyribonucleotides adenine (A), guanine (G), thymine (T) and/or cytosine (C) (modified or rare nucleotides can also be used). When in a double-stranded form, it can comprise or include a "regulatory element" according to the present invention, as the term is defined herein. The term "oligonucleotide" or "DNA" can be found in linear DNA molecules or fragments, viruses, plasmids, vectors, chromosomes or synthetically derived DNA. As used herein, particular double-stranded DNA sequences may be described according to the normal convention of giving only the sequence in the 5' to 3' direction. It will also be recognized that "oligonucleotide" can be (and usually are) in a single-stranded form.

Probes of the invention can be utilized with naturally occurring sugar-phosphate backbones as well as modified backbones including phosphorothioates, dithionates, alkyl phosphonates and α-nucleotides and the like. Modified sugar-phosphate backbones are generally taught by Miller, 1988, Ann. Reports Med. Chem. 23:295 and Moran et al., 1987, Nucleic acid molecule. Acids Res., 14:5019. Probes of the invention can be constructed of either ribonucleic acid (RNA) or deoxyribonucleic acid (DNA), and preferably of DNA.

The types of detection methods in which probes can be used include Southern blots (DNA detection), dot or slot blots (DNA, RNA), and Northern blots (RNA detection). Although less preferred, labeled proteins could also be used to detect a particular nucleic acid sequence to which it binds. More recently, PNAs have been described (Nielsen et al. 1999, Current Opin. Biotechnol. 10:71–75). PNAs could also be used to detect the mRNAs of the present invention. Other detection methods include kits containing probes on a dipstick setup and the like.

Although the present invention is not specifically dependent on the use of a label for the detection of a particular nucleic acid sequence, such a label might be beneficial, by increasing the sensitivity of the detection. Furthermore, it enables automation. Probes can be labeled according to numerous well known methods (Sambrook et al., 1989, supra). Non-limiting examples of labels include $^{3}H$, $^{14}C$, $^{32}P$, and $^{35}S$. Non-limiting examples of detectable markers include ligands, fluorophores, chemiluminescent agents, enzymes, and antibodies. Other detectable markers for use with probes, which can enable an increase in sensitivity of the method of the invention, include biotin and radionucleotides. It will become evident to the person of ordinary skill that the choice of a particular label dictates the manner in which it is bound to the probe.

As commonly known, radioactive nucleotides can be incorporated into probes of the invention by several methods. Non-limiting examples thereof include kinasing the 5' ends of the probes using gamma $^{32}P$ ATP and polynucleotide kinase, using the Klenow fragment of Pol I of E. coli in the presence of radioactive dNTP (i.e. uniformly labeled DNA probe using random oligonucleotide primers in low-melt gels), using the SP6/T7 system to transcribe a DNA segment in the presence of one or more radioactive NTP, and the like.

As used herein, "oligonucleotides" or "oligos" define a molecule having two or more nucleotides (ribo or deoxyribonucleotides). The size of the oligo will be dictated by the particular situation and ultimately on the particular use thereof and adapted accordingly by the person of ordinary skill. An oligonucleotide can be synthesised chemically or derived by cloning according to well known methods.

As used herein, a "primer" defines an oligonucleotide which is capable of annealing to a target sequence, thereby creating a double stranded region which can serve as an initiation point for DNA synthesis under suitable conditions.

Amplification of a selected, or target, nucleic acid sequence may be carried out by a number of suitable methods. See generally Kwoh et al., 1990, Am. Biotechnol. Lab. 8:14–25. Numerous amplification techniques have been described and can be readily adapted to suit particular needs of a person of ordinary skill. Non-limiting examples of amplification techniques include polymerase chain reaction (PCR), ligase chain reaction (LCR), strand displacement amplification (SDA), transcription-based amplification, the Qβ replicase system and NASBA (Kwoh et al., 1989, Proc. Natl. Acad. Sci. USA 86, 1173–1177; Lizardi et al., 1988, BioTechnology 6:1197–1202; Malek et al., 1994, Methods Mol. Biol., 28:253–260; and Sambrook et al., 1989, supra). Preferably, amplification will be carried out using PCR.

Polymerase chain reaction (PCR) is carried out in accordance with known techniques. See, e.g., U.S. Pat. Nos. 4,683,195; 4,683,202; 4,800,159; and 4,965,188 (the disclosure of all three U.S. Patents are incorporated herein by reference). In general, PCR involves, a treatment of a nucleic acid sample (e.g., in the presence of a heat stable DNA polymerase) under hybridizing conditions, with one oligonucleotide primer for each strand of the specific sequence to be detected. An extension product of each primer which is synthesized is complementary to each of the two nucleic acid strands, with the primers sufficiently complementary to each strand of the specific sequence to hybridize therewith. The extension product synthesized from each primer can also serve as a template for further synthesis of extension products using the same primers. Following a sufficient number of rounds of synthesis of extension products, the sample is analysed to assess whether the sequence or sequences to be detected are present. Detection of the amplified sequence may be carried out by visualization following EtBr staining of the DNA following gel electrophores, or using a detectable label in accordance with known techniques, and the like. For a review on PCR techniques (see PCR Protocols, A Guide to Methods and Amplifications, Michael et al. Eds, Acad. Press, 1990).

As used herein, the term "gene" is well known in the art and relates to a nucleic acid sequence defining a single protein or polypeptide. A "structural gene" defines a DNA sequence which is transcribed into RNA and translated into a protein having a specific amino acid sequence thereby giving rise the a specific polypeptide or protein. It will be readily recognized by the person of ordinary skill, that the nucleic acid sequence of the present invention can be incorporated into anyone of numerous established kit formats which are well known in the art.

A "heterologous" (i.e. a heterologous gene) region of a DNA molecule is a subsegment segment of DNA within a larger segment that is not found in association therewith in nature. The term "heterologous" can be similarly used to define two polypeptidic segments not joined together in nature. Non-limiting examples of heterologous genes include reporter genes such as luciferase, chloramphenicol acetyl transferase, beta-galactosidase, growth hormone, green fluorescent protein (U.S. Pat. No. 5,968,8750) and the like which can be juxtaposed or joined to heterologous control regions or to heterologous polypeptides. In accordance with one embodiment and in particular for the screening assays, such a reporter gene can enable a quantification of the PCA3$^{dd3}$ promoter activity. Preferably the heterologous sequence encodes a therapeutic sequence.

The term "vector" is commonly known in the art and defines a plasmid DNA, phage DNA, viral DNA and the like, which can serve as a DNA vehicle into which DNA of the present invention can be cloned. Numerous types of vectors exist and are well known in the art.

The term "expression" defines the process by which a gene is transcribed into mRNA (transcription), the mRNA is then being translated (translation) into one polypeptide (or protein) or more.

The terminology "expression vector" defines a vector or vehicle as described above but designed to enable the expression of an inserted sequence following transformation into a host. The cloned gene (inserted sequence) is usually placed under the control of control element sequences such as promoter sequences. The placing of a cloned gene under such control sequences is often referred to as being operably linked to control elements or sequences.

Operably linked sequences may also include two segments that are transcribed onto the same RNA transcript. Thus, two sequences, such as a promoter and a "reporter sequence" or "therapeutic sequence" are operably linked if transcription commencing in the promoter will produce an RNA transcript of the reporter sequence or therapeutic sequence. In order to be "operably linked" it is not necessary that two sequences be immediately adjacent to one another.

Expression control sequences will vary depending on whether the vector is designed to express the operably linked gene in a prokaryotic or eukaryotic host or both (shuttle vectors) and can additionally contain transcriptional elements such as enhancer elements, termination sequences, tissue-specificity elements, and/or translational initiation and termination sites. In accordance with a preferred embodiment of the present invention, the promoter sequences of the present invention find utility in the expression of a heterologous sequence in a prostate cell or more preferably a prostate cancer cell. Of course, the present invention also finds utility in a prostate cancer tissue-derived cell (e.g. metastasis).

The DNA construct can be a vector comprising a promoter that is operably linked to an oligonucleotide sequence of the present invention, which is in turn, operably linked to a heterologous gene, such as the gene for the luciferase reporter molecule. "Promoter" refers to a DNA regulatory region capable of binding directly or indirectly to RNA polymerase in a cell and initiating transcription of a downstream (3' direction) coding sequence. For purposes of the present invention, the promoter is bound at its 3' terminus by the transcription initiation site and extends upstream (5' direction) to include the minimum number of bases or elements necessary to initiate transcription at levels detectable above background. Within the promoter will be found a transcription initiation site (conveniently defined by mapping with S1 nuclease), as well as protein binding domains (consensus sequences) responsible for the binding of RNA polymerase. Eukaryotic promoters will often, but not always, contain "TATA" boxes and "CCAT" boxes.

As used herein, the designation "functional derivative" denotes, in the context of a functional derivative of a sequence whether an nucleic acid or amino acid sequence, a molecule that retains a biological activity (either function or structural) that is substantially similar to that of the original sequence. This functional derivative or equivalent may be a natural derivative or may be prepared synthetically. Such derivatives include more precisely PCA3$^{dd3}$ sequences having substitutions, deletions, or additions of one or more nucleotides (duplications), provided that the promoter activity and the prostate-specific activity thereof are conserved. The term "functional derivatives" is intended to include "fragments", "segments", "variants" "analogs" or "chemical derivatives" of the subject matter of the present invention.

Thus, the term "variant" refers herein to a nucleic acid molecule which is substantially similar in structure and biological activity to the nucleic acid of the present invention.

The functional derivatives of the present invention can be synthesized chemically or produced through recombinant DNA technology. All these methods are well known in the art.

One skilled in the art will realize that genomes often contain slight allelic variations between individuals. Therefore, the isolated nucleic acid molecule is also intended to include allelic variations, so long as the sequence is a functional derivative of the PCA3$^{dd3}$ promoter sequence. When a PCA3 allele does not encode the identical sequence to that found in SEQ ID No:1, it can be isolated and identified as a PCA3$^{dd3}$ promoter using the same techniques used herein, and especially PCR techniques to amplify the appropriate region with primers based on the sequences disclosed herein.

As used herein, "chemical derivatives" is meant to cover additional chemical moieties not normally part of the subject matter of the invention. Such moieties could affect the physico-chemical characteristic of the derivative (i.e. solubility, absorption, half life and the like, decrease of toxicity). Such moieties are exemplified in Remington's Pharmaceutical Sciences (1980). Methods of coupling these chemical-physical moieties to a polypeptide are well known in the art.

The term "allele" defines an alternative form of a gene which occupies a given locus on a chromosome.

As commonly known, a "mutation" is a detectable change in the genetic material which can be transmitted to a daughter cell. As well known, a mutation can be, for example, a detectable change in one or more deoxyribonucleotide. For example, nucleotides can be added, deleted, substituted for, inverted, or transposed to a new position. Spontaneous mutations and experimentally induced mutations exist. The result of a mutation(s) of nucleic acid molecule is a mutant nucleic acid molecule. A mutant polypeptide can be encoded from this mutant nucleic acid molecule.

As used herein, the term "purified" refers to a molecule having been separated from a cellular component. Thus, for example, a "purified protein" has been purified to a level not found in nature. A "substantially pure" molecule is a molecule that is lacking in all other cellular components.

As used herein, the terms "molecule", "compound", or "agent" are used interchangeably and broadly to refer to natural, synthetic or semi-synthetic molecules or compounds. The term "molecule" therefore denotes for example chemicals, macromolecules, cell or tissue extracts (from plants or animals) and the like. Non limiting examples of molecules include nucleic acid molecules, peptides, ligands, antibodies, carbohydrates and pharmaceutical agents. The agents can be selected and screened by a variety of means including random screening, rational selection and by rational design using for example protein or ligand modelling methods such as computer modelling. The terms "rationally selected" or "rationally designed" are meant to define compounds which have been chosen based on the configuration of the interaction domains of the present invention. As will be understood by the person of ordinary skill, macromolecules having non-naturally occurring modifications are also within the scope of the term "molecule". For example, peptidomimetics, well known in the pharmaceutical industry and generally referred to as peptide analogs can be generated by modelling as mentioned above. The molecules identified in accordance with the teachings of the present invention have a therapeutic value in diseases or conditions in which the physiology or homeostasis of the prostate cell and/or tissue or cell derived therefrom is compromised. In a preferred embodiment, the defect of the cell or tissue is associated with a defect in the expression of PCA3 mRNAs. Alternatively, the molecules identified in accordance with the teachings of the present invention find utility in the development of compounds which can modulate the activity of the PCA3$^{dd3}$ promoter sequences.

The present invention also provides antisense nucleic acid molecules which can be used for example to decrease or abrogate the activity of the PCA3$^{dd3}$ promoter. An antisense nucleic acid molecule according to the present invention refers to a molecule capable of forming a stable duplex or triplex with a portion of its targeted nucleic acid sequence (DNA or RNA). The use of antisense nucleic acid molecules and the design and modification of such molecules is well known in the art as described for example in WO 96/32966, WO 96/11266, WO 94/15646, WO 93/08845 and U.S. Pat. No. 5,593,974. Antisense nucleic acid molecules according to the present invention can be derived from the nucleic acid sequences and modified in accordance to well known methods. For example, some antisense molecules can be designed to be more resistant to degradation to increase their affinity to their targeted sequence, to affect their transport to chosen cell types or cell compartments, and/or to enhance their lipid solubility by using nucleotide analogs and/or substituting chosen chemical fragments thereof, as commonly known in the art.

An indicator cell in accordance with the present invention can be used to identify antagonists. For example, the test molecule or molecules are incubated with the host cell in conjunction with one or more agonists held at a fixed concentration. An indication and relative strength of the antagonistic properties of the molecule(s) can be provided by comparing the level of gene expression in the indicator cell in the presence of the agonist, in the absence of test molecules versus in the presence thereof. Of course, the antagonistic effect of a molecule can also be determined in the absence of agonist, simply by comparing the level of expression of the reporter gene product in the presence and absence of the test molecule(s).

It shall be understood that the "in vivo" experimental model can also be used to carry out an "in vitro" assay. For example, cellular extracts from the indicator cells can be prepared and used in one of the aforementioned "in vitro" tests.

As used herein the recitation "indicator cells" refers to cells that contain a PCA3$^{dd3}$ promoter sequence operably linked to a detectable heterologous sequence. In some embodiment, the protein encoded by the heterologous sequence can be coupled to an identifiable or selectable phenotype or characteristic. Such indicator cells can be used in the screening assays of the present invention. In certain embodiments, the indicator cells have been engineered so as to express a chosen derivative, fragment, homolog, or mutant of the PCA3$^{dd3}$ promoter of the present invention. The cells must be chosen so as to enable a detectable promoter activity of the PCA3$^{dd3}$ promoter. Preferably, the cell is a prostate cell, more preferably the prostate cell is a prostate cancer cell.

For certainty, the sequences and polypeptides useful to practice the invention include without being limited thereto mutants, homologs, subtypes, alleles and the like. It shall be understood that generally, the sequences of the present invention should encode a functional (albeit defective) PCA3$^{dd3}$ promoter. It will be clear to the person of ordinary skill that whether the PCA3$^{dd3}$ promoter sequence of the present invention, variant, derivative, or fragment thereof retains its promoter activity can be readily determined by using the teachings and assays of the present invention and the general teachings of the art.

As exemplified herein below, the PCA3$^{dd3}$ promoter of the present invention can be modified, for example by in vitro mutagenesis (e.g. point mutations, Example 6) or by deletion analysis (Example 4), to dissect the structure-function relationship thereof and permit a better design and identification of modulating compounds.

A host cell or indicator cell has been "transfected" by exogenous or heterologous DNA (e.g. a DNA construct) when such DNA has been introduced inside the cell. The transfecting DNA may or may not be integrated (covalently linked) into chromosomal DNA making up the genome of the cell.

A stably transfected cell is one in which the transfecting DNA has become integrated into a chromosome so that it is inherited by daughter cells through chromosome replication. This stability is demonstrated by the ability of the eukaryotic cell to establish cell lines or clones comprised of a population of daughter cells containing the transfecting DNA. Transfection methods are well known in the art (Sambrook et al., 1989, supra; Ausubel et al., 1994 supra).

From the specification and appended claims, the term therapeutic agent should be taken in a broad sense so as to also include a combination of at least two such therapeutic agents. Further, the DNA segments or proteins according to the present invention can be introduced into individuals in a number of ways. For example, prostatic cells can be isolated from the afflicted individual, transformed with a DNA construct according to the invention and reintroduced to the afflicted individual in a number of ways. Alternatively, the DNA construct can be administered directly to the afflicted individual. The DNA construct can also be delivered through a vehicle such as a liposome, which can be designed to be targeted to a specific cell type, and engineered to be administered through different routes.

For administration to humans, the prescribing medical professional will ultimately determine the appropriate form and dosage for a given patient, and this can be expected to vary according to the chosen therapeutic regimen (i.e. DNA construct, protein, cells), the response and condition of the patient as well as the severity of the disease.

Composition within the scope of the present invention should contain the active agent (i.e. recombinant vector, nucleic acid, and molecule) in an amount effective to achieve the desired therapeutic effect while avoiding adverse side effects. Typically, the nucleic acids in accordance with the present invention can be administered to mammals (i.e. humans) in doses ranging from 0.005 to 1 mg per kg of body weight per day of the mammal which is treated. Pharmaceutically acceptable preparations and salts of the active agent are within the scope of the present invention and are well known in the art (Remington's Pharmaceutical Science, 16th Ed., Mack Ed.). For the administration of polypeptides, antagonists, agonists and the like, the amount administered should be chosen so as to avoid adverse side effects. The dosage will be adapted by the clinician in accordance with conventional factors such as the extent of the disease and different parameters from the patient. Typically, 0.001 to 50 mg/kg/day will be administered to the mammal.

The present invention also relates to a kit comprising the oligonucleotide primer of the present invention, which are specific to either one of the PCA3 mRNA lacking the additional sequence of the present invention or the PCA3 mRNA containing the additional sequence of the present invention.

The present invention thus provides the means to specifically express a heterologous sequence of interest into prostate cells or prostate-derived cell and more particularly in prostate cancer cells. Thus, the present invention provides the means to directly or indirectly correct a disease state in a prostate or prostate-derived cell. The highly prostate specific expression of the PCA3$^{dd3}$ promoter is herein demonstrated.

Thus, in accordance with a preferred embodiment of the present invention, there is provided a method of expressing specifically in prostate cells or prostate-derived cells, a chosen heterologous sequence, and preferably a therapeutic sequence, capable of directly or indirectly improving the diseased state in the prostate cell or prostate-derived cells. In a particularly preferred embodiment, the present invention provides the means to specifically kill prostate cancer cells or prostate cancer-derived cells, through an introduction thereinto of a recombinant vector comprising a PCA3$^{dd3}$ promoter sequence of the present invention, operably linked to a suicide gene.

Further objects and advantages of the present invention will be clear from the description that follows.

BRIEF DESCRIPTION OF THE DRAWINGS

Having thus generally described the invention, reference will now be made to the accompanying drawings, showing by way of illustration a preferred embodiment thereof, and in which:

FIG. 1 shows the nucleotide sequence of the PCA3$^{dd3}$ promoter and exon 1 regions (SEQ ID NO:1). (A) Restriction map of PCA3$^{dd3}$ genomic clones pFS28, pGV61, and pME4.6. The location of exon 1 is indicated by a shaded box. (B) Nucleotide sequence of the genomic region surrounding the transcription start site (position 1, *) of the PCA3$^{dd3}$ gene. The exon 1 sequence is underlined. Potential transcription factor binding sites are identified by the Mat-Inspector program using the TRANSFAC 3.5 matrices (Quandt et al., Nucleic Acids Res. 1995), with a core similarity of 1.00 and a matrix similarity of over 0.90, and are indicated by boxes. Abbreviations: CCAAT: CAAT-box; C/EBPbeta: CCAAT/enhancer binding protein beta; E-box: bHLH binding site; FKHL: forkhead homologue; FREAC: forkhead related activator; NF-1: nuclear factor 1; Th1/E47: Thing1/E47 (bHLH) heterodimer;

FIG. 3 shows the results of two complementary experiments (Primer extension analysis and RNase protection assay) for the determination of the PCA3$^{dd3}$ transcription start site. (A) Primer extension analysis of the PCA3$^{dd3}$ 5'-flanking region. Twenty micrograms of total RNA from prostatic adenocarcinoma (lanes 4, 5, 7, 8, and 9), liver (lane 3 and 10), or lung (lanes 2 and 11) tissue or tRNA (lanes 1 and 6) were used for primer extension using oligonucleotides BUS7 (lanes 1–5) and BUS2 (lanes 6–11) as primers as indicated. Primer extension products are indicated by arrows (←, BUS2, and ←//+, BUS7 products). A DNA sequence ladder of the PCA3$^{dd3}$ genomic clone pME1.5S3 primed with BUS7 was used as a size marker. (B) For RNase (S1 nuclease) protection analysis, a 252-bp radiolabeled single-stranded DNA probe was synthesized from plasmid pME4.6, containing exon 1 of PCA3$^{dd3}$ and it's 5'-flanking region, using BUS21 as a primer. The HincII-digested probe was hybridized to 40 micrograms total RNA from prostatic adenocarcinoma (lanes 1–4), liver (lane 5), or lung (lane 6) tissue or tRNA (lane 7) and treated with S1 nuclease at 37° C. (lanes 1–7) or at 30° C. (data not shown). Arrows mark protected fragments. A DNA sequence ladder of the PCA3$^{dd3}$ genomic clone pME4.6 primed with BUS21 was used as a size marker;

Other objects, advantages and features of the present invention will become more apparent upon reading of the following non-restrictive description of preferred embodiments with reference to the accompanying drawing which is exemplary and should not be interpreted as limiting the scope of the present invention.

DESCRIPTION OF THE PREFERRED EMBODIMENT

PCA3$^{dd3}$ gene has been shown to be sensitive and specific marker for diagnosis and prostate cancer in a patient. The characterization of its promoter, sequence deposited into the GenBank™ data base, opens the way to the specific expression of heterologous sequence in a prostate or prostate-derived cell and more particularly prostate cancer cells and to development of therapies against prostate cancer.

The present invention is illustrated in further detail by the following non-limiting examples.

EXAMPLE 1

Isolation and Sequence Analysis of PCA3$^{dd3}$ Promoter Clones

Genomic clones lambdaFIX-ME3, -ME4 and -IH1, containing the 5' end of the human PCA3$^{dd3}$ cDNA were obtained previously (Bussemakers, PCT/CA98/00346 1998; and Bussemakers et al., Cancer Res. 1999a). Lambda phage DNA was endonuclease digested and subcloned in plasmid vectors pGEM-3Zf(+) or pT$_2$. Double stranded plasmid DNA was isolated by standard procedures, and sequenced using the Thermo Sequenase cycle sequencing kit (Amersham) and Texas Red labeled universal primers. Sequencing products were separated and analyzed using the Vistra DNA Sequencer 725.

In FIG. 1A, a restriction map is shown of the resulting clones pFS28, pGV61 and pME4.6, containing PCA3$^{dd3}$ exon 1 and its 5'-flanking sequences. The nucleotide sequence of the 5'-flanking region was determined (FIG. 1B) and is deposited in the GenBank database under GenBank Accession Number AF279290. Comparison of the PCA3$^{dd3}$ 5'-flanking nucleotide sequence with sequences in the non-redundant nucleotide databases and the eukaryotic promoter database, using BLAST (Altschul et al., Nucleic Acids Res. 1997), revealed no homology to any gene, c.q. promoter sequences described. Identification of potential transcription factor (TF) binding sites by the MatInspector program, using the TRANSFAC 3.5 matrices (Quandt et al., Nucleic Acids Res. 1995), revealed no canonical binding sites at consensus positions, i.e. no initiator nor TATA boxes could be identified. Only a single CAAT element at a non-consensus position (−374 to −378) was found. Other potential TF binding sites are shown in FIG. 1B.

The structure function relationship of the PCA3$^{dd3}$ promoter had thus to be dissected using molecular biology methods as shown below.

EXAMPLE 2

Figure 2:
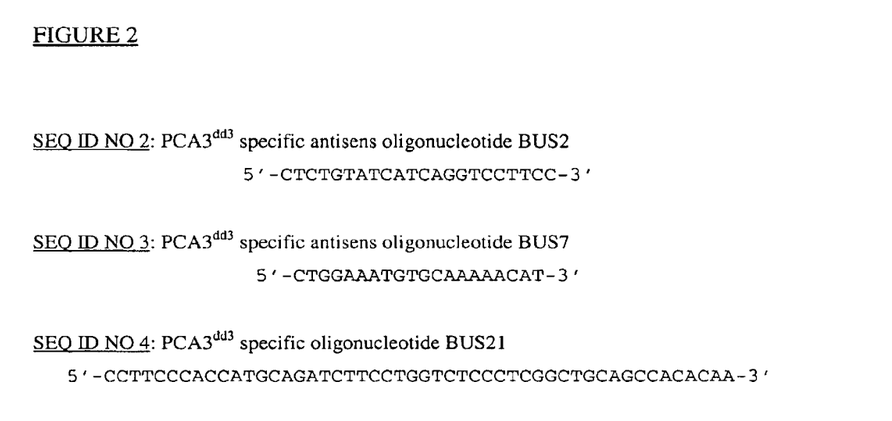
FIG. 2 shows the nucleotide sequences of the specific oligonucleotides (SEQ ID NO:2 to SEQ ID NO:4) used in the determination of the PCA3$^{dd3}$ transcription start site. BUS2 and BUS7 sequences are PCA3$^{dd3}$ specific antisense oligonucleotides used for primer extension analysis. The BUS21 sequence is a PCA3$^{dd3}$ specific oligonucleotide used for RNase protection assay.

Sequences of the Oligonucleotides used in the Determination of the PCA3$^{dd3}$ Transcription Start Site The nucleotide sequences of the specific oligonucleotides used in the determination of the PCA3$^{dd3}$ transcription start site are shown in FIG. 2 (SEQ ID NO:2 to SEQ ID NO:4). BUS2 (SEQ ID NO:2) and BUS7 (SEQ ID NO:3) sequences are PCA3$^{dd3}$ specific antisense oligonucleotides used for primer extension analysis. The BUS21 (SEQ ID NO:4) sequence is a PCA3$^{dd3}$ specific oligonucleotide used for RNase protection assay.

EXAMPLE 3

Determination of the PCA3$^{dd3}$ Start Site

The isolated human PCA3$^{dd3}$ cDNAs were shown to possess different 5' ends, associated with their different lengths (Bussemakers et al., Cancer Res. 1999a). In order to precisely define the PCA3$^{dd3}$ transcription start site, primer extension analysis and RNase protection assays, using total RNA from human prostate cancer tissue and normal human liver and lung tissue as a negative control, were performed.

For the primer extension analysis, PCA3$^{dd3}$ exon 1 (BUS2) and exon 3 (BUS7)-specific oligonucleotides were used as a primer. The use of the exon 3-specific primer, BUS7, is validated, since exon 2 is present in only a minority of transcripts (<5%) due to alternative splicing (Bussemakers et al., Cancer Res. 1999a). Briefly, total RNA of human tissue was isolated using guanidium isothiocyanate by standard procedures. PCA3$^{dd3}$ -specific antisense oligonucleotides BUS2 (5'-CTCTGTATCATCAGGTCC-TTCC-3', position +120 to +99) and BUS7 (5'-CTGGAA-ATGTGCAAAAACAT-3', position +420 to +401) were [gamma-$^{32}$P]ATP end-labeled (3000 mCi/mmol, Amersham) and annealed with 20 micrograms of RNA at 30° C. in 30 microliters hybridization buffer (40 mM PIPES pH 6.7, 1 mM EDTA, 0.5 M NaCl, 80% formamide). Primers were extended with 200 units of SuperScript II-MMLV reverse transcriptase (Gibco BRL) in 25 microliters RT buffer (Gibco BRL), supplemented with 0.5 mM dNTPs, 10 mM DTT, 0.5 micrograms actinomycin D, and 1 unit/microliter RNase inhibitor, for 1.5 hours at 42° C. RNase A-treated primer extension products were resolved by 6% polyacrylamide-urea gel electrophoresis. PCA3$^{dd3}$ genomic sequence ladders generated with the same oligonucleotide primers were used as size markers. Gels were dried and exposed to Hyperfilm (Amersham) using two amplifying screens at −80° C. for approximately three days.

For the RNase protection assay, a DNA fragment encompassing the presumed transcription start site was used as a probe. A 517 bps Sau3AI DNA fragment from clone pME4.6 was ligated into the BamHI site of M13mp18. Single-stranded M13 DNA was isolated, annealed with the PCA3$^{dd3}$ exon 1-specific oligonucleotide BUS21 (5'-CCT-TCCCACCATGCAGATCTTCCTGGTCTCCCTCGGC-TGCAGCCACACAA-3'), and extended using [gamma-$^{32}$P] dATP and Klenow DNA polymerase. The radiolabeled probe was linearized with HincII and purified from a denaturing 5% polyacrylamide-urea gel. All reactions were performed according to standard protocols. The probe (10$^5$ cpm) was annealed overnight with 40 micrograms total RNA at 30° C. in 30 microliters hybridization buffer (40 mM PIPES pH 6.7, 1 mM EDTA, 0.5 M NaCl, 80% formamide). DNA-RNA hybrids were digested with 300 units S1 nuclease (Amersham) in 300 microliters S1 buffer (0.28 M NaCl, 0.05 M NaAc pH 4.5, 4.5 mM ZnSO$_4$, supplemented with 20 micrograms/ml single-stranded herring sperm DNA) for 60 minutes at 30° C. or 37° C. Digestions were stopped by the addition of stop buffer (4 M NH$_4$Ac, 50 mM EDTA, 50 micrograms/ml tRNA). Protected DNA fragments were resolved by 6% polyacrylamide-urea gel electrophoresis. A PCA3$^{dd3}$ genomic sequence ladder generated with the BUS21 primer was used as size marker. Gels were dried and exposed to Hyperfilm (Amersham) using two amplifying screens at −80° C. for approximately three days.

Figure 3:
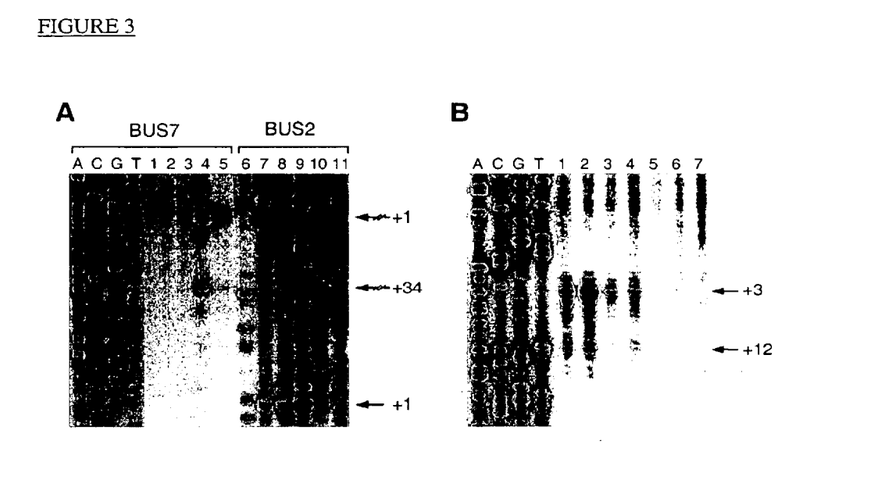
Figure 4:
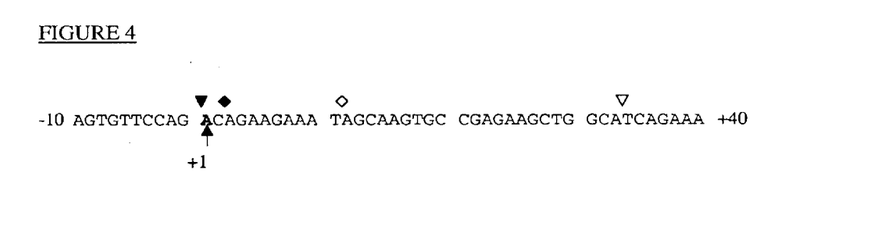
FIG. 4 shows the nucleotide sequence surrounding the PCA3$^{dd3}$ transcription start site (SEQ ID NO:5). Primer extension products are indicated by triangles (closed triangle, major start site; open triangle, minor site), and S1 nuclease protected fragments by diamonds (closed diamond, major start site; open diamond, minor site)

The results of a representative experiment for the primer extension analysis are shown in FIG. 3A. Two prostate-specific extension products could be identified in FIG. 3A (lanes 4, 5, 7, 8 and 9). The transcription start site deduced from the longest extension product was designated +1, and consequently, the smaller fragment was initiated from an alternative start site at position +34. As shown in FIG. 3B, RNase protection analysis, using S1 nuclease, revealed two prostate-specific S1-protected fragments (FIG. 3B, lanes 1 to 4). The most abundant product was initiated from position +3 with respect to the transcription start site identified by primer extension analysis (position +1). The minor S1 protected fragment, was initiated from an alternative start site at position +12. The identified major and minor transcription start sites are shown above the PCA3$^{dd3}$ nucleotide sequence in FIG. 4.

EXAMPLE 4

Transcriptional Activity of the Human PCA3$^{dd3}$ Promoter

In order to demonstrate promoter activity, the PCA3$^{dd3}$ 5'-flanking region was cloned upstream of the human growth hormone (hGH) reporter gene (construct pDDGH-1.9, position −433 to +62, 28 to 522 in SEQ ID NO:1). Briefly, the promoterless plasmid pOGH (Nichols Institute) was used for cloning PCA3$^{dd3}$ promoter fragments into the polylinker upstream of the human growth hormone gene. PCA3$^{dd3}$ promoter fragments were produced by PCR, using 5' HindIII-tagged and 3' BamHI-tagged primers and normal human genomic DNA as a template. Subsequently, the fragments were cleaved with HindIII and BamHI and cloned into pOGH, using standard procedure. Mutant promoter constructs were generated using the "GeneEditor" in vitro site-directed mutagenesis system (Promega). Since the hGH secretion capacity of different cell lines may vary, for each cell line the activity of the PCA3$^{dd3}$-hGH constructs was compared to that of plasmid pTKGH containing the human growth hormone gene driven by the constitutive promoter of the HSV-thymidine kinase gene (Selden et al., Mol. Cell. Biol. 1986).

Then, these constructs were used in transient transfection of the two following cell lines: PC-346C, a derivative of the human prostate adenocarcinoma cell lines LNCaP (kindly provided by Dr. W. van Weerden; Dept. of Urology, Erasmus University Rotterdam, The Netherlands) and TSU-pr1. Both cell lines were grown in RPMI 1640 medium, supplemented with 10% foetal calf serum (Gibco BRL), in an atmosphere of 5% $CO_2$ and 37° C. For transient transfection, LNCaP cells were seeded at a density of $1 \times 10^6$ cells per 10-cm dish two days prior to transfection and TSU-pr1 cells were seeded at a density of $5 \times 10^5$ cells per 10-cm dish one day before transfection. For each transfection 3 micrograms of the appropriate PCA3$^{dd3}$-hGH construct and 2.3 micrograms pCH110 (internal marker) were complexed with Fugene-6 reagent (Boeringer Mannheim) in serum-free medium for 15 minutes at room temperature. The Fugene-6/DNA complexes were added to the cell cultures, and cells were grown for an additional 72 hours. Transfections were performed at least three times in duplica. After transfection, medium was collected and stored at −20° C. until use. Human growth hormone secretion in the medium was determined using the two-site fluoroimmunometric Delfia hGH assay kit (Wallac Oy, Turku, Finland), according to the manufacturer's instructions. hGH values were normalized to the beta-galactosidase activities measured in the corresponding cell extracts. hGH values and relative induction values are expressed as mean and standard error of the mean (SEM).

When pDDGH-1.9 was transfected into LNCaP cells, a human prostate carcinoma cell line expressing PCA3$^{dd3}$ mRNA, weak promoter activity was seen (FIG. 5), i.e. hGH production was about 20% of the HSV-tk driven hGH production. Promoters are known to function unidirectionally. Therefore, the pDDGH-1.9 promoter sequences were cloned in the reverse orientation upstream of the hGH gene (pDDGH-2.1, pos. +62 to −433). This pDDGH-2.1 promoter construct was inactive in LNCaP cells, moreover, the hGH production was below that found in cells transfected with the promoterless pOGH construct. Sequences upstream of the 500-bps PCA3$^{dd3}$ promoter (−433 to +62) had no effect on the PCA3$^{dd3}$ promoter activity (FIG. 5, construct pDDGH-1.5, pos. −1,900 to +62).

To investigate whether regions within the 500-bps PCA3$^{dd3}$ promoter contributed to PCA3$^{dd3}$ promoter activity, a series of 5' deletion constructs were generated. Transfection of the deletion constructs pDDGH-1.10, -1.11 and -1.12 into LNCaP cells resulted in an increased promoter activity, compared to the activity observed in pDDGH-1.9 (FIG. 5). Construct pDDGH-1.12 (pos. −152 to +62) displayed the highest PCA3$^{dd3}$ promoter activity of all constructs tested. Shortening the latter construct led to a decreased promoter activity (pDDGH-1.16) and a complete loss of activity in construct pDDGH-1.18 (pos. −41 to +62).

EXAMPLE 5
Cell-Type Specificity of PCA3$^{dd3}$ Promoter Activity

To define the specificity of the observed PCA3$^{dd3}$ promoter activity, promoter constructs pDDGH-1.9, displaying basal activity, and pDDGH-1.12, displaying maximum activity, were transfected into cell lines of different tissue origin. Then, the production of human growth hormone was measured in each cell line. The protocol for these experiments was described in Example 4. The different cell lines used for these experiments were as follow: PC-346C, a derivative of the human prostate adenocarcinoma cell line LNCaP; TSU-pr1, a human prostate cancer cell line; SW800, a human bladder cancer cell line; HT29, a human colon carcinoma cell line; SKRC-7, a renal cell carcinoma cell line and A431, a vulval epidermoid cancer cell line.

Figure 6:
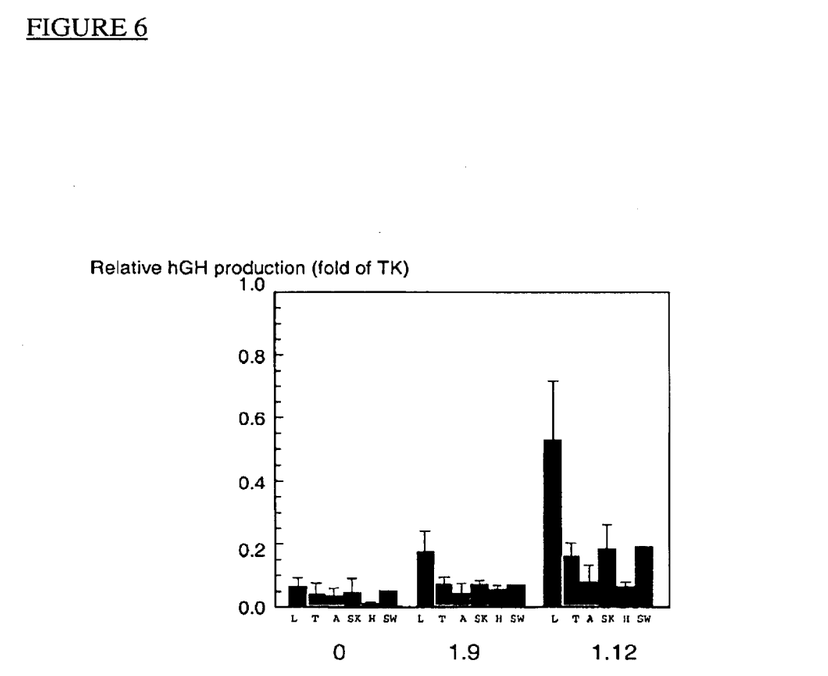
FIG. 6 illustrates the specificity of the PCA3$^{dd3}$ promoter activity in cell lines from different tissue origin. The pDDGH-1.9 and pDDGH-1.12 PCA3$^{dd3}$-promoter constructs were transiently transfected into LNCaP (L), TSU-pr1 (T), A431 (A), SKRC-7 (SK), HT-29 (H), and SW800 (SW) cells. PCA3$^{dd3}$ promoter activity, i.e. hGH production, was determined as described in FIG. 5.

PCA3$^{dd3}$ promoter activity of pDDGH-1.9 was found in LNCAP cells (FIG. 6), but not in A431 (vulval carcinoma), HT-29 (colon carcinoma), SKRC-7 (renal cell carcinoma) and SW800 (bladder carcinoma) cells. Importantly, this promoter construct is also silent in prostate carcinoma cell lines that do not express PCA3$^{dd3}$ mRNA (TSU-pr1, FIG. 6, and PC-3, data not shown). The increased promoter activity of the truncated promoter construct pDDGH-1.12, however, was also observed in the PCA3$^{dd3}$-negative cell lines, although the maximum promoter activity was significantly lower than in LNCAP cells.

EXAMPLE 6
Site Directed Mutagenesis and Effects on PCA3$^{dd3}$ Promoter Activity In order to further dissect the PCA3$^{dd3}$ promoter element and to identify the potential significance of the promoter activity, several base substitution mutants in the reporter constructs pDDGH-1.9 and pDDGH-1.12 were created. Base substitutions were introduced in those motifs that were predicted by the MatInspector program, using the TRANSFAC 3.5 matrices (Quandt et al., Nucleic Acids Res. 23:4878–4884 (1995)), with a core similarity of 1.00 and a matrix similarity of over 0.90 (see FIG. 1B). The positions and nature of the base substitutions are shown in FIG. 7A. Promoter mutants were transiently transfected into LNCaP cells. Then hGH production and promoter activities were measured as described in Example 4. Base substitutions in the proximal region of the promoter clearly reduced its activity (FIG. 7B). Mutations in the NF-1 sequence motif (between −61 to −60) reduced promoter activity of the 1.9/60a (SEQ ID NO:7) and 1.12/60a constructs to 27% and 18% respectively, and mutations in the E-box motif (between −35 to −33) reduced transcription from reporter constructs 1.9/60c (SEQ ID NO:8) and 1.12/60c to 43% and 67% respectively. These data show that the proximal region of PCA3$^{dd3}$ promoter is functionally involved in the initiation of transcription of this gene, corroborating the 5' deletion analysis, shown in FIG. 5 and the significant decrease in promoter activity of the −89 to +62 construct (pDDGH-1.16) and the silencing of the promoter activity in the −41 to +62 construct (pDDGH-1.18). As well, these results highlight region −70 to −30 (391 to 431 of SEQ ID NO:1) as harboring sequences having a significant prostate-specific promoter activity.

The PCA3$^{dd3}$ gene was previously shown to be highly overexpressed in the majority of prostatic adenocarcinomas (Bussemakers et al., Cancer Res. 59:5975–5979 (1999)). These data suggest that PCA3$^{dd3}$ mRNA expression is regulated by a unique prostate-cancer-specific transcriptional mechanism. Nucleotide sequence analysis did not reveal any obvious promoter elements.

No known initiator motif, no TATA-box, no CAAT-box, and no GC-rich regions were found at consensus positions within the PCA3$^{dd3}$ promoter. In addition, the PCA3$^{dd3}$ promoter initiates transcription mainly at a single site, but lacks characterized initiator elements. A few TATA-less promoters have been described that show the properties of the PCA3$^{dd3}$ promoter, initiator-less and not GC-rich (Brakebusch et al., J. Biol. Chem. 272:3674–3682 (1997)).

In any event, the data herein presented suggest that the PCA3$^{dd3}$ gene promoter is tissue and cell-type specific and, therefore, is a genuine prostate-cancer-specific promoter. The absolute promoter activities of the PCA3$^{dd3}$ promoter constructs tested, however, are rather low compared to the HSV-tk promoter activity. This correlates with the low level of endogenous PCA3$^{dd3}$ mRNA expression observed in LNCaP cells, in contrast to the high PCA3$^{dd3}$ expression in prostate cancer cells.

CONCLUSION

In conclusion, the present invention shows the cloning and the initial characterization of the PCA3$^{dd3}$ gene promoter. This promoter could be an interesting tool for therapeutic application.

Although the present invention has been described hereinabove by way of preferred embodiments thereof, it can be modified without departing from the spirit and nature of the subject invention as defined in the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. An isolated promoter sequence comprising a sequence as set forth between nucleotide positions 372 to 460 of SEQ ID NO:1.

2. The isolated promoter sequence of claim 1, wherein said sequence is selected from the group consisting of:
   a) 372 to 461 of SEQ ID NO:1;
   b) 372 to 522 of SEQ ID NO:1;
   c) 309 to 460 of SEQ ID NO:1;
   d) 309 to 461 of SEQ ID NO:1;
   e) 309 to 522 of SEQ ID NO:1;
   f) 207 to 460 of SEQ ID NO:1;
   g) 207 to 461 of SEQ ID NO:1;
   h) 207 to 522 of SEQ ID NO:1;
   i) 95 to 460 of SEQ ID NO:1;
   j) 95 to 461 of SEQ ID NO:1;
   k) 95 to 522 of SEQ ID NO:1;
   l) 28 to 460 of SEQ ID NO:1;
   m) 28 to 461 of SEQ ID NO:1;
   n) 28 to 522 of SEQ ID NO:1;
   o) 1 to 460 of SEQ ID NO:1;
   p) 1 to 461 of SEQ ID NO:1; and
   q) 1to 522 of SEQ ID NO:1.

3. A vector comprising the sequence of claim 1.

4. A vector comprising the sequence of claim 2.

5. A cell comprising the vector of claim 3.

6. A cell comprising the vector of claim 4.

7. A method of modulating the transcription of a heterologous sequence in a prostate cell, comprising: a) joining of said heterologous sequence downstream of said sequence of claim 1 so as to subject said heterologous sequence to the control of said promoter sequence; and b) assessing the level of transcription of said heterologous sequence.

8. A method of modulating an expression of a transcript in a prostate cancer cell, comprising an administration in said cell of an antisense molecule capable of modulating a transcriptional activity of said sequence of claim 1.

9. A method of identifying an agent which modulates an expression of a transcript in a prostate cell, comprising an assessment of a transcriptional activity of a promoter sequence which comprises a sequence as set forth between nucleotide positions 372 to 460 of SEQ ID NO:1, in the presence, versus the absence of a candidate compound, wherein an agent which modulates said transcriptional activity of said promoter sequence is selected when said transcriptional activity is significantly different in the presence of said compound, as compared to in the absence thereof.

10. The method of claim 9, wherein said prostate cell is a prostate cancer cell.

11. The vector of claim 3, further comprising a heterologous sequence operably linked to said promoter sequence, wherein said heterologous sequence is selected from a sequence which encodes a reporter gene and a therapeutic sequence.

12. A vector comprising a promoter sequence as set forth between nucleotide positions 372 to 460 of SEQ ID NO:1, operably linked to a heterologous therapeutic sequence, wherein an expression of said therapeutic sequence inhibits the growth or kills a cell in which it is expressed.

13. The vector of claim 12, wherein said therapeutic sequence is a suicide gene.

14. The vector of claim 13, further comprising an enhancer element.

15. A method for diagnosing prostate cancer or a predisposition thereto in a nucleic acid prostatic sample of a patient comprising assessing in said sample, the promoter activity of said promoter sequence of claim 1, wherein an active state of said promoter sequence, as compared to an inactive state thereof, indicates a cancerous state of said prostatic sample or a predisposition of said sample to develop into a cancerous state.

* * * * *

SEQUENCE LISTING

<160> NUMBER OF SEQ ID NOS: 8

<210> SEQ ID NO 1
<211> LENGTH: 580
<212> TYPE: DNA
<213> ORGANISM: Homo sapiens

<400> SEQUENCE: 1

```
cactagagga gcaccttagg aattgacctg tggatctcaa cttcgttagg gttaaaagat    60
tatttgttgg gcaagggtag gaccaataac ctcattcaca atgcattcat tgattcgttg   120
attcacagag caaatacttc tgaacaactc ctgtgtttct ggcactgttc taggcaccag   180
tgatatagga gccaacaaga cagacatgtc actgctctca tggagctgca tttcagtgca   240
tggaggcaga aaacaaacaa acaaatalaat aaataaataa ataaataaga taatttttaa   300
tagcaacgtg tcaacatagt gtgacgggaa ggagcatgat gagacagaag gaaggtttaa   360
actgggaaat ctgagaaatg gtatggttgt atgtgggttg gcattcttgc atgatgggag   420
tggccacctg ctttcatatt ctgaagtcag agtgttccag acagaagaaa tagcaagtgc   480
cgagaagctg gcatcagaaa aacagagggg agatttgtgt ggctgcagcc gagggagacc   540
aggaagatct gcatggtggg aaggacctga tgatacagag                         580
```

<210> SEQ ID NO 2
<211> LENGTH: 22
<212> TYPE: DNA
<213> ORGANISM: Artificial Sequence
<220> FEATURE:
<223> OTHER INFORMATION: Oligonucleotide

<400> SEQUENCE: 2

```
ctctgtatca tcaggtcctt cc                                             22
```

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide

```
<400> SEQUENCE: 3
ctggaaatgt gcaaaaacat                                             20

<210> SEQ ID NO 4
<211> LENGTH: 50
<212> TYPE: DNA
<213> ORGANISM: Artificial Sequence
<220> FEATURE:
<223> OTHER INFORMATION: Oligonucleotide

<400> SEQUENCE: 4
ccttcccacc atgcagatct tcctggtctc cctcggctgc agccacacaa             50

<210> SEQ ID NO 5
<211> LENGTH: 50
<212> TYPE: DNA
<213> ORGANISM: Artificial Sequence
<220> FEATURE:
<223> OTHER INFORMATION: Oligonucleotide

<400> SEQUENCE: 5
agtgttccag acagaagaaa tagcaagtgc cgagaagctg gcatcagaaa             50

<210> SEQ ID NO 6
<211> LENGTH:
<212> TYPE:
<213> ORGANISM:

<400> SEQUENCE: 6

<210> SEQ ID NO 7
<211> LENGTH: 522
<212> TYPE: DNA
<213> ORGANISM: Homo sapiens

<400> SEQUENCE: 7
cactagagga gcaccttagg aattgacctg tggatctcaa cttcgttagg gttaaaagat  60
tatttgttgg gcaagggtag gaccaataac ctcattcaca atgcattcat tgattcgttg  120
attcacagag caaatacttc tgaacaactc ctgtgtttct ggcactgttc taggcaccag  180
tgatatagga gccaacaaga cagacatgtc actgctctca tggagctgca tttcagtgca  240
tggaggcaga aaacaaacaa acaaataaat aaataaataa ataaataaga taattttttaa  300
tagcaacgtg tcaacatagt gtgacgggaa ggagcatgat gagacagaag gaaggtttaa  360
actgggaaat ctgagaaatg gtatggttgt atgtgggttc acattcttgc atgatgggag  420
tggccacctg ctttcatatt ctgaagtcag agtgttccag acagaagaaa tagcaagtgc  480
cgagaagctg gcatcagaaa aacagagggg agatttgtgt gg                    522

<210> SEQ ID NO 8
<211> LENGTH: 522
<212> TYPE: DNA
<213> ORGANISM: Homo sapiens

<400> SEQUENCE: 8
cactagagga gcaccttagg aattgacctg tggatctcaa cttcgttagg gttaaaagat  60
tatttgttgg gcaagggtag gaccaataac ctcattcaca atgcattcat tgattcgttg  120
attcacagag caaatacttc tgaacaactc ctgtgtttct ggcactgttc taggcaccag  180
tgatatagga gccaacaaga cagacatgtc actgctctca tggagctgca tttcagtgca  240
```

```
                                              -continued tggaggcaga  aaacaaacaa  acaaataaat  aaataaataa  ataaataaga  taatttttaa      300
tagcaacgtg  tcaacatagt  gtgacgggaa  ggagcatgat  gagacagaag  gaaggtttaa      360
actgggaaat  ctgagaaatg  gtatggttgt  atgtgggttg  gcattcttgc  atgatgggag      420
tggccgtatg  ctttcatatt  ctgaagtcag  agtgttccag  acagaagaaa  tagcaagtgc      480
cgagaagctg  gcatcagaaa  aacagagggg  agatttgtgt  gg                          522
```